US012624049B2

(12) United States Patent
Bray et al.

(10) Patent No.: US 12,624,049 B2
(45) Date of Patent: May 12, 2026

(54) SALT AND CRYSTAL FORMS OF 4-AMINO-5-(6-(4-METHYLPIPERAZIN-1-YL)-1H-BENZO[D]IMIDAZOL-Z-YL) THIENO[2.3-B]PYRIDIN-6(7H)-ONE

(71) Applicant: UNIVERSITY HEALTH NETWORK, Toronto (CA)

(72) Inventors: Mark R. Bray, Oakville (CA); Sze-Wan Li, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 694 days.

(21) Appl. No.: 17/924,220

(22) PCT Filed: May 10, 2021

(86) PCT No.: PCT/CA2021/050645
§ 371 (c)(1),
(2) Date: Nov. 9, 2022

(87) PCT Pub. No.: WO2021/226707
PCT Pub. Date: Nov. 18, 2021

(65) Prior Publication Data

US 2023/0174549 A1 Jun. 8, 2023

Related U.S. Application Data

(60) Provisional application No. 63/022,867, filed on May 11, 2020.

(51) Int. Cl.

| | |
|---|---|
| ***C07D 495/04*** | (2006.01) |
| ***A61K 45/06*** | (2006.01) |
| ***A61P 35/00*** | (2006.01) |
| ***C07C 59/255*** | (2006.01) |

(52) U.S. Cl.
CPC ............ *C07D 495/04* (2013.01); *A61K 45/06* (2013.01); *A61P 35/00* (2018.01); *C07C 59/255* (2013.01); *C07B 2200/13* (2013.01)

(58) Field of Classification Search
CPC .... C07B 2200/13; C07D 495/04; A61P 35/00
See application file for complete search history.

(56) References Cited

U.S. PATENT DOCUMENTS

| | | | |
|---|---|---|---|
| 2011/0076291 | A1 | 3/2011 | Blaquiere et al. |
| 2012/0203002 | A1 | 8/2012 | Zhang et al. |

FOREIGN PATENT DOCUMENTS

| | | | |
|---|---|---|---|
| CN | 102239171 | A | 11/2011 |
| CN | 102341402 | A | 2/2012 |
| CN | 103003283 | A | 3/2013 |
| CN | 107922431 | A | 4/2018 |
| CN | 109721620 | A | 5/2019 |
| JP | 2018-522858 | A | 8/2018 |
| WO | 2016/205942 | A1 | 12/2016 |

OTHER PUBLICATIONS

International Search Report and Written Opinion for Application No. PCT/CA2021/050645, dated Aug. 10, 2021, 7 pages.
Gould, Salt selection for basic drugs. International Journal of Pharmaceutics. 1986;33:201-217.
Stahly, On the importance of selecting salts for pharmaceutical crystals and screening for crystal polymorphisms. Journal of Pharmaceutical Science and Technology, Japan. 2006;66(6):435-439.

*Primary Examiner* — Brenda L Coleman
*Assistant Examiner* — Madeline E Braun
(74) *Attorney, Agent, or Firm* — McCarter & English, LLP; Wei Song

(57) ABSTRACT

A novel salt form of Compound (I) represented by the following structural formula, and its corresponding pharmaceutical compositions, are disclosed.

(I)

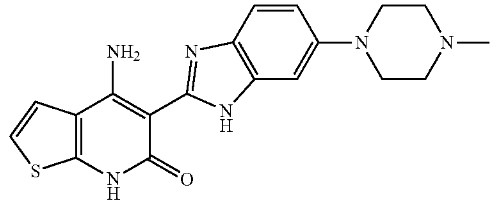

,

Particular single crystalline forms of 1:1 Compound (I) tartrate salt are characterized by a variety of properties and physical measurements. Methods of preparing specific crystalline forms are also disclosed. The present disclosure also provides methods of treating cancer in a subject.

12 Claims, 6 Drawing Sheets

SALT AND CRYSTAL FORMS OF 4-AMINO-5-(6-(4-METHYLPIPERAZIN-1-YL)-1H-BENZO[D]IMIDAZOL-Z-YL)THIENO [2.3-B]PYRIDIN-6(7H)-ONE

CROSS-REFERENCE TO RELATED APPLICATIONS

This application is a 35 U.S.C. § 371 national stage filing of of International Application No. PCT/CA2021/050645, filed May 10, 2021, which claims priority to U.S. Provisional Application No. 63/022,867, filed May 11, 2020. The entire contents of the aforementioned applications are incorporated herein by reference.

BACKGROUND

Hematopoietic progenitor kinase 1 (HPK1) is a hematopoietic cell-restricted Ste20 serine/threonine kinase. It has been reported that HPK1 can be a novel target for cancer immunotherapy (Sawasdikosol et al., *Immunol Res.* 2012 December; 54(1-3):262-5). Specifically, targeted disruption of HPK1 alleles confers T cells with an elevated Th1 cytokine production in response to TCR engagement. HPK1 (−/−) T cells proliferate more rapidly than the haplotype-matched wild-type counterpart and are resistant to prostaglandin E2 (PGE(2))-mediated suppression. Most strikingly, mice that received adoptive transfer of HPK1 (−/−) T cells became resistant to lung tumor growth. Also, the loss of HPK1 from dendritic cells (DCs) endows them with superior antigen presentation ability, enabling HPK1 (−/−) DCs to elicit a more potent anti-tumor immune response when used as cancer vaccine.

U.S. Pat. No. 10,501,474, the entire teachings of which are incorporated herein by reference, discloses highly potent inhibitors of HPK1. The structure of one of the inhibitors disclosed in U.S. Pat. No. 10,501,474, referred to herein as "Compound (I)" is shown below:

Compound (I)

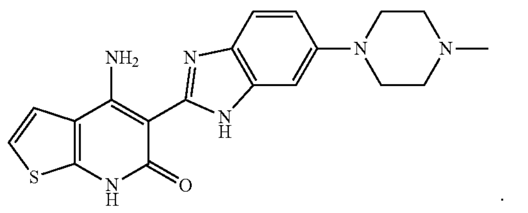

The chemical name of Compound (I) is 4-amino-5-(6-(4-methylpiperazin-1-yl)-1H-benzo[d]imidazol-2-yl)thieno[2,3-b]pyridin-6(7H)-one.

The successful development of pharmaceutically active agents, such as Compound (I), typically requires the identification of a solid form with properties that enable ready isolation and purification following synthesis, that are amendable to large scale manufacture, that can be stored for extended periods of time with minimal absorption of water, decomposition or transformation into other solid forms, that are suitable for formulation and that can be readily absorbed following administration to the subject (e.g., are soluble in water and in gastric fluids).

SUMMARY

The present disclosure relates to a tartrate salt of Compound (I), wherein the molar ratio between Compound (I) and tartaric acid is 1:1. Because of the two carboxylic acid groups on tartaric acid and the multiple basic nitrogen atoms in Compound (I), multiple possible stoichiometries are possible. For example, Compound (I) forms both a 1:1 tartaric acid salt and a 1:0.5 tartaric acid salt. The 1:1 tartaric acid salt of Compound (I) is referred to herein as "1:1 Compound (I) tartrate" or "1:1 Compound (I) tartrate salt".

It has now also been found that 1:1 Compound (I) tartrate salt can be crystallized under well-defined conditions to provide non-hygroscopic crystalline forms (see Example 6). The tartrate salt also has improved solubility in water and in simulated gastric fluids (see Example 7 and Table 7), has an extended shelf life (see Example 8), and is suitable for large scale synthesis (see Example 5).

A salt screening with thirteen different acids (see Examples 1 to 3) with different Compound (I)/acid molar ratios was performed. Among 20 obtained salt forms (Examples 1 and 2), only mono hydrochloric, mesylate, tartrate and maleate salts showed modest to good crystallinity by X-ray powder diffraction (XRPD). Further evaluation of these four salts in different solvent system shows that the crystallinity of the mesylate and maleate salts is modest (see Example 3). In addition, different polymorphic forms were isolated for mono hydrochloric, mesylate, and maleate salts when different solvent systems were used. Notably, the di-hydrochloric salt does not have or has very low crystallinity as demonstrated in Examples 1 and 4.

Compared to the mono hydrochloric salt, 1:1 Compound (I) tartrate salt has the additional advantage that it is non-hygroscopic. Moreover, as shown in Example 9 below, compared to the free base and the mono HCl salt, the 1:1 Compound (I) tartrate salt in crystalline form results in improved plasma concentrations in dogs, following oral administration. This is a significant advantage because the new solid form can be administered orally to result in effective plasma levels of the drug.

In one aspect, the present disclosure provides a tartrate salt of Compound (I), wherein the molar ratio between Compound (I) and tartaric acid is 1:1.

In another aspect, the present disclosure provides a pharmaceutical composition comprising 1:1 Compound (I) tartrate salt and a pharmaceutically acceptable carrier or diluent.

In yet another aspect, the present disclosure provides a method of treating a subject with cancer, comprising administering to the subject an effective amount of 1:1 Compound (I) tartrate salt disclosed herein or the corresponding pharmaceutical composition.

The present disclosure also provides a method of treating a subject with cancer, comprising administering to the subject an effective amount of 1:1 Compound (I) tartrate salt disclosed herein or the corresponding pharmaceutical composition, and an effective amount of an immunomodulatory agent such as a checkpoint inhibitor (e.g., anti-PD-1 antibody, anti-CTLA-4 antibody or anti-PD-L1 antibody) or an inhibitor of tryptophan oxidation (e.g. IDO1, IDO2 or TDO2 inhibitor). In one example, the immunomodulatory agent is anti-PD-1 antibody.

In one alternative, the 1:1 Compound (I) tartrate salt or the corresponding pharmaceutical composition is administered with an effective amount of one or more other anti-cancer therapies, and preferably in combination with PD-1 inhibitor. In one embodiment, The PD-1 inhibitor is nivolumab, pembrolizumab, pidilizumab, BMS 936559, MPDL3280A, MSB0010718C or MEDI4736. In one specific embodiment, the PD-1 inhibitor is nivolumab. In one specific embodiment, the PD-1 inhibitor is pembrolizumab.

The present disclosure also provides a use of the 1:1 Compound (I) tartrate salt disclosed herein or the corresponding pharmaceutical composition comprising the same in any of the methods described above. In one embodiment, provided is the 1:1 Compound (I) tartrate salt or a pharmaceutical composition thereof comprising the same for use in any of the methods described herein. In another embodiment, provided is use of the 1:1 Compound (I) tartrate salt or a pharmaceutical composition thereof comprising the same for the manufacture of a medicament for any of the methods described herein.

DETAILED DESCRIPTION

The present disclosure is directed to a novel tartrate salt (i.e., 1:1 tartrate salt) of Compound (I), as well as polymorphic forms of the foregoing.

In one embodiment, tartrate salt (i.e., 1:1 tartrate salt) of Compound (I) is crystalline.

As used herein, "crystalline" refers to a solid having a crystal structure wherein the individual molecules have a highly homogeneous regular locked-in chemical configuration. Crystalline Compound (I) salt can be crystals of a single crystal form of Compound (I) salt, or a mixture of crystals of different single crystalline forms. A single crystal form means Compound (I) salt as a single crystal or a plurality of crystals in which each crystal has the same crystal form.

For the crystalline forms of Compound (I) disclosed herein, at least a particular percentage by weight of 1:1 Compound (I) tartrate salt is in a single crystal form. Particular weight percentages include 85%, 86%, 87%, 88%, 89%, 90%, 91%, 92%, 93%, 94%, 95%, 96%, 97%, 98%, 99%, 99.5%, 99.9%, or a weight percentage of 70%-75%, 75%-80%, 80%-85%, 85%-90%, 90%-95%, 95%-100%, 70-80%, 80-90%, 90-100% by weight of the Compound (I) salt is in a single crystal form. It is to be understood that all values and ranges between these values and ranges are meant to be encompassed by the present disclosure.

When the crystalline Compound (I) salt is defined as a specified percentage of one particular crystal form of the Compound (I) salt, the remainder is made up of amorphous form and/or crystal forms other than the one or more particular forms that are specified. Examples of single crystal forms include 1:1 Compound (I) tartrate salt characterized by one or more properties as discussed herein.

Figure 6:
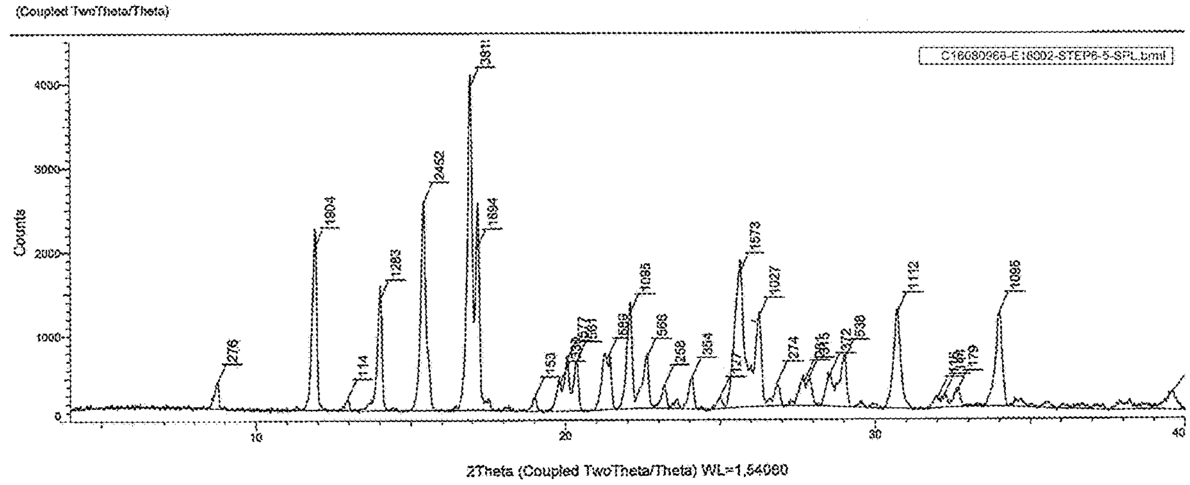
FIG. 6 shows the X-ray Powder Diffraction (XRPD) pattern of 1:1 Compound (I) tartrate salt obtained from Example 5.

The crystalline Compound (I) salts disclosed herein exhibit strong, unique XRPD patterns with sharp peaks corresponding to angular peak positions in 2θ and a flat baseline, indicative of a highly crystalline material (e.g., FIG. 6). The XRPD patterns disclosed in the present application are obtained from a copper radiation source (Cu Kα1; λ=1.54179 Å).

Characterization of 1:1 Compound (I) Tartrate Salt Crystalline Forms

In one embodiment, 1:1 Compound (I) tartrate salt is characterized by an X-ray powder diffraction pattern which comprises peaks at 11.9°, 15.4°, 16.9°, and 17.2°±0.2 in 2θ. In another embodiment, 1:1 Compound (I) tartrate salt is characterized by an X-ray powder diffraction pattern which comprises at least three peaks chosen from 11.9°, 15.4°, 16.9°, 17.2°, and 25.6°±0.2 in 2θ. In another embodiment, 1:1 Compound (I) tartrate salt is characterized by an X-ray powder diffraction pattern which comprises peaks at 11.9°, 15.4°, 16.9°, 17.2°, and 25.6°±0.2 in 2θ. In another embodiment, 1:1 Compound (I) tartrate salt is characterized by an X-ray powder diffraction pattern which comprises peaks at 11.9°, 14.0°, 15.4°, 16.9°, 17.2°, 25.6°, 26.3, and 30.7°±0.2 in 2θ. In yet another embodiment, 1:1 Compound (I) tartrate salt is characterized by an X-ray powder diffraction pattern which comprises peaks at 11.9°, 14.0°, 15.4°, 16.9°, 17.2°, 22.1°, 25.6°, 26.3, 30.7°, and 34.0°±0.2 in 2θ. In another embodiment, 1:1 Compound (I) tartrate salt is characterized by an X-ray powder diffraction pattern as identified above and further comprises peaks at 8.7° and 12.9°±0.2 in 2θ. In yet another embodiment, 1:1 Compound (I) tartrate salt is characterized by an X-ray powder diffraction pattern substantially similar to FIG. 6.

As used herein, an X-ray powder diffractogram is "substantially similar to that in [a particular] Figure" when at least 90%, such as at least 95%, at least 98%, or at least 99%, of the signals in the two diffractograms are the same±0.2 in 2θ. In determining "similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported±0.2 degrees 2θ of the reported value, an art-recognized variance as discussed below.

It is well known in the crystallography art that, for any given crystal form, an angular peak position may vary slightly due to factors such as temperature variation, sample displacement, and the presence or absence of an internal standard. In the present disclosure, the variability of an angular peak position is ±0.2 in 2θ. In addition, the relative peak intensities for a given crystal form may vary due to differences in crystallite sizes and non-random crystallite orientations in sample preparation for XRPD analysis. It is well known in the art that this variability will account for the above factors without hindering the unequivocal identification of a crystal form.

In another embodiment, 1:1 Compound (I) tartrate salt is characterized by differential scanning calorimeter (DSC) peak phase transition temperatures of 189±2° C.

In another embodiment, 1:1 Compound (I) tartrate salt is characterized by a hygroscopicity measurement, wherein water uptake is less than 4% (e.g. 2% or 1%) of the mass of the tartrate salt at 90% relative humidity (RH); or less than 2% (e.g. 1% or 0.5%) of the mass of the tartrate salt at 60% RH; or less than 1% (e.g. 0.5% or 0.1%) of the mass of the tartrate salt at 30% RH. The hygroscopicity in different relative humidity (RH) is measured under following conditions:

i) drying between 0.5 and 1.5 mg of the tartrate salt under a nitrogen atmosphere at 0% relative humidity for 2 hours;

ii) increasing or decreasing the relative humidity in steps of 10% from 0% to 90% then to 0%;

iii) maintaining the relative humidity at each step until the mass change compared to the mass of the original tartrate salt per minute is less than 0.01 (%/min), provided that minimum and maximum duration time at each step is 10 minutes and 180 minutes, respectively; and iv) measuring the mass of the tartrate salt at the desired relative humidity (e.g., 90%, 60%, or 30%) and wherein steps i)-iv) are carried out at 25° C.

The hygroscopicity is measured using standard methods, e.g., those described in G. Zografi and M. J. Kontny, "Sorption of water by solids" in Physical Characterization of Pharmaceutical Solids, ed. H. G. Brittain, Marcel Dekker, New York, NY (1995), pp. 385-418, or the procedure described in Example 6 in the present disclosure.

Characterization of 1:1 Compound (I) Mono Hydrochloride Salt Crystalline Forms

Figure 1:
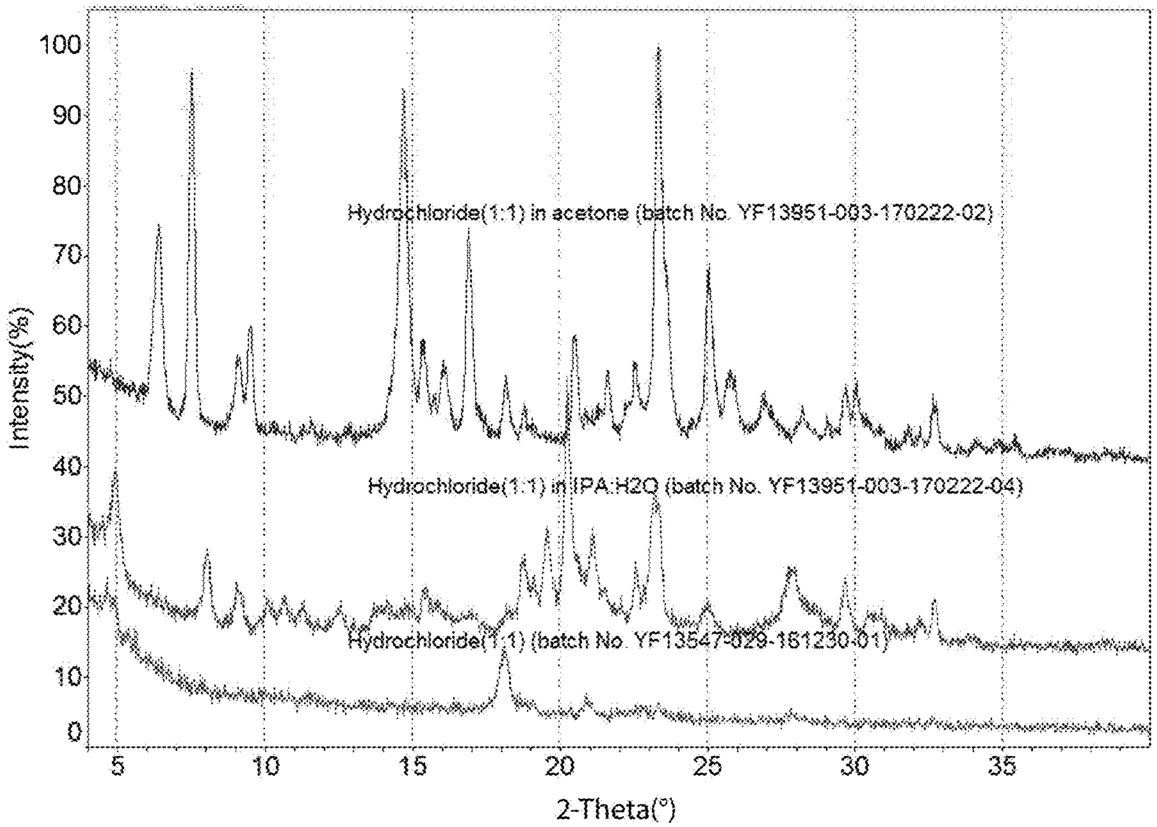
FIG. 1 shows the X-ray Powder Diffraction (XRPD) patterns of 1:1 Compound (I) hydrochloride salt obtained from different examples. The bottom spectrum is for the hydrochloride salt obtained from Example 1 (Batch 1). The middle spectrum is for the hydrochloride salt obtained from Example 3 using IPA:water (Batch 2). The top spectrum is for the hydrochloride salt obtained from Example 3 using acetone (Batch 3).

In one embodiment, 1:1 Compound (I) mono hydrochloride salt is a single crystalline form, characterized by an X-ray powder diffraction pattern substantially similar to top spectrum of FIG. 1.

Pharmaceutical Compositions

Pharmaceutical compositions of the disclosure comprise 1:1 Compound (I) tartrate salt, or a crystalline form thereof described herein and one or more pharmaceutically acceptable carrier(s) or diluent(s). The term "pharmaceutically acceptable carrier" refers to a pharmaceutically acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the subject. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the disclosure may be administered orally, parenterally, by inhalation spray, topically, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In an embodiment, the compositions of the disclosure are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions, or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present disclosure that may be combined with the carrier to produce a composition in a single dosage form will vary depending upon the host treated, the particular mode of administration, and other factors determined by the person administering the single dosage form.

Dosages

Toxicity and therapeutic efficacy of a salt of Compound (I), or a crystalline form thereof described herein, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. A salt of Compound (I), or a crystalline form thereof that exhibits large therapeutic indexes are preferred. While a salt of Compound (I), or a crystalline form thereof described herein that exhibits toxic side effects may be used, care should be taken to design a delivery system that targets such salt or crystalline form to the site of affected tissue in order to minimize potential damage to uninfected cells and, thereby, reduce side effects.

Data obtained from the cell culture assays and animal studies can be used in formulating a range of dosage for use in humans. The dosage of such salts or crystalline forms may lie within a range of circulating concentrations that include the $ED_{50}$ with little or no toxicity. The dosage may vary within this range depending upon the dosage form employed and the route of administration utilized. For any salt of Compound (I), or a crystalline form thereof described herein, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular subject will depend upon a variety of factors, including but not limited to the activity of the specific compound employed, the age, body weight, general health, sex, diet, time of administration, rate of excretion, drug combination, and the judgment of the treating physician and the severity of the particular disease being treated. The amount of a salt of Compound (I), or a crystalline form of the present disclosure in the composition will also depend upon the particular compound in the composition.

Methods of Treatment

A “subject” is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein, “treating a subject with a cancer” includes achieving, partially or substantially, one or more of the following: arresting the growth, reducing the extent of the cancer (e.g., reducing size of a tumor), inhibiting the growth rate of the cancer, ameliorating or improving a clinical symptom or indicator associated with the cancer (such as tissue or serum components) or increasing longevity of the subject; and reducing the likelihood of recurrence of the cancer.

The term an “effective amount” means an amount when administered to the subject which results in beneficial or desired results, including clinical results, e.g., inhibits, suppresses or reduces the cancer (e.g., as determined by clinical symptoms or the amount of cancer cells) in a subject as compared to a control.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

In an embodiment, an effective amount of a compound taught herein ranges from about 0.1 to about 1000 mg/kg body weight, alternatively about 1 to about 500 mg/kg body weight. In another embodiment, an effective amount of a compound taught herein ranges from about 0.5 to about 5000 $mg/m^2$, alternatively about from 5 to about 2500 $mg/m^2$, and in another alternative from about 50 to about 1000 $mg/m^2$. The skilled artisan will appreciate that certain factors may influence the dosage required to effectively treat a subject suffering from cancer or reduce the likelihood of recurrence of a cancer. These factors include, but are not limited to, the severity of the disease or disorder, previous treatments, the general health and/or age of the subject and other diseases present.

A “treatment” regime of a subject with an effective amount of the compound of the present disclosure may consist of a single administration, or alternatively comprise a series of applications. For example, 1:1 Compound (I) tartrate salt may be administered at least once a week. However, in another embodiment, the compound may be administered to the subject from about one time per week to once daily for a given treatment. The length of the treatment period depends on a variety of factors, such as the severity of the disease, the age of the subject, the concentration and the activity of the compounds of the present disclosure, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

Compound (I), its salt and crystal forms disclosed herein inhibit HPK1. Thus, generally, compounds described herein are useful in the treatment of diseases or conditions associated with such kinases.

In an embodiment, the disclosure provides a method of inhibiting HPK1 activity in a subject in need of inhibition of HPK1 activity, comprising administering to the subject an effective amount of Compound (I), or the tartrate salt (e.g., 1:1 Compound (I) tartrate salt), crystal form or pharmaceutical composition described herein.

Because of their activity against HPK1, Compound (I), or the tartrate salt (e.g., 1:1 Compound (I) tartrate salt), crystal form or pharmaceutical composition described herein can be used to treat a subject with a condition associated with aberrant HPK1 activity.

In an embodiment, the condition associated with aberrant HPK1 activity is cancer.

Cancers that can be treated (including reduction in the likelihood of recurrence) by the methods of the present teachings include breast cancer, colorectal cancer, lung cancer, ovarian cancer, uterine cancer, prostate cancer, leukemia, lymphomas, brain cancer (including glioblastoma multiforme and neuroblastoma), head and neck cancer, pancreatic cancer, melanoma, hepatocellular carcinoma, renal cancer, and soft tissue sarcomas. In one embodiment, the cancer is breast cancer, colon cancer, and ovarian cancer. In one embodiment, the cancer is selected from leukemia, acute myeloid leukemia, chronic myelogenous leukemia, breast cancer, brain cancer, colon cancer, colorectal cancer, head and neck cancer, hepatocellular carcinoma, lung adenocarcinoma, metastatic melanoma, pancreatic cancer, prostate cancer, ovarian cancer and renal cancer. In one embodiment, the cancer is lung cancer, colon cancer, brain cancer, neuroblastoma, prostate cancer, melanoma, glioblastoma multiforme or ovarian cancer. In another embodiment, the cancer is lung cancer, breast cancer, colon cancer, brain cancer, neuroblastoma, prostate cancer, melanoma, glioblastoma multiforme or ovarian cancer. In yet another embodiment, the cancer is breast cancer, colon cancer and lung cancer. In another embodiment, the cancer is a breast cancer. In yet another embodiment, the cancer is a basal sub-type breast cancer or a luminal B sub-type breast cancer. In yet another embodiment, the cancer is a basal sub-type breast cancer. In yet another embodiment, the basal sub-type breast cancer is ER (estrogen receptor), HER2 and PR (progesterone receptor) negative breast cancer. In yet another embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibemoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

The present teachings also provide methods of treating a subject with a disease comprising administering to the subject an effective amount of a compound represented by Structural Formula (I) in combination with an effective immunomodulatory therapy (also referred as immunotherapy). Immunotherapy is the treatment of disease by using an immunomodulatory agent to induce, enhance, or suppress an immune response. Immunotherapies designed to elicit or amplify an immune response are classified as activation immunotherapies, while immunotherapies that reduce or suppress are classified as suppression immunotherapies. The disease described herein is a cancer.

Immunomodulatory therapies, used alone or in combination approaches, include i) immune checkpoint blockade inhibitors, including but not limited to anti-CTLA-4 (cytotoxic T-lymphocyte-associated protein 4) antibodies (e.g. Ipilimumab), agents that disrupt the PD-1/PD-L1 and PD-L2 interaction, e.g. Nivolumab (Opdivo®-Bristol Myers Squibb), Pembrolizumab (Keytruda®, KM-3475, Merck), Pidilizumab (CT-011, Cure Tech), BMS 936559 (BMS) and MPDL3280A (Roche); and other immune response inhibitory receptors e.g. anti-CD47; ii) cell based therapies (including, but not limited to, dendritic cell therapy (e.g. Sipuleucel T (Provenge®)) and adoptive T-cell therapies), iii) vaccination strategies; iv) Adoptive T-cell therapy; v) agents that prevent metabolic inhibition of the immune response, including inhibitors of indoleamine 2, 3-dioxygenase (e.g. INCB024360 (Incyte), 1-methyl-D-tryptophan, indoximod (NewLink Genetics)) or arginase; and vi) cytokine-based therapy, e.g., interferons (in particular type I interferon) and interleukins (e.g. interleukin-2).

In one embodiment, the immunomodulatory agent used for the immunomodulatory therapy is a PD-1 inhibitor, for example, an anti-PD1 antibody.

Programmed cell death protein 1, also known as PD-1 and CD279 (cluster of differentiation 279), is a protein that in humans is encoded by the PDCD1 gene. PD-1 is a cell surface receptor that belongs to the immunoglobulin superfamily and is expressed on T cells and pro-B cells. PD-1 binds two ligands, PD-L1 and PD-L2, both of which are members of the B7 family.

PD-1 and its ligands play an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells).

The PD-1 inhibitor used in the present invention includes, but is not limited to, nivolumab, pembrolizumab, pidilizumab, BMS 936559, MPDL3280A, MSB0010718C or MEDI4736. Among them, BMS 936559, MPDL3280A, MSB0010718C, and MEDI4736 bind ligand PD-L1, all of which are antibodies. Both nivolumab and pembrolizumab are approved by the Food and Drug Administration for treatment of unresectable or metastatic melanoma which no longer responds to other drugs.

Vaccination strategies include anti-microbial immunotherapy, which includes vaccination, involves activating the immune system to respond to an infectious agent.

Adoptive T-cell therapy uses T cell-based cytotoxic responses to attack cancer cells. T cells that have a natural or genetically engineered reactivity to a patient's cancer are generated in vitro and then transferred back into the cancer patient. One study using autologous tumor-infiltrating lymphocytes was an effective treatment for patients with metastatic melanoma. This can be achieved by taking T cells that are found with the tumor of the patient, which are trained to attack the cancerous cells. These T cells are referred to as tumor-infiltrating lymphocytes (TIL) are then encouraged to multiply in vitro using high concentrations of IL-2, anti-CD3 and allo-reactive feeder cells. These T cells are then transferred back into the patient along with exogenous administration of IL-2 to further boost their anti-cancer activity.

The present teachings also provide methods of treating a subject with a cancer comprising administering to the subject an effective amount of Compound (I), or the tartrate salt (e.g., 1:1 Compound (I) tartrate salt), crystal form or pharmaceutical composition described herein in combination with an effective anti-cancer therapy. In one embodiment, the cancer is a metastatic cancer. A "metastatic cancer" is a cancer that has spread from its primary site to other parts of the body.

The anti-cancer therapy described herein includes co-administration of an effective amount of a second anti-cancer agent together with a disclosed HPK-1 inhibitor. An "anti-cancer agent" is a compound, which when administered in an effective amount to a subject with cancer, can achieve, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

The anti-cancer agents suitable for use in the methods described herein include any anti-cancer agents that have been approved for the treatment of cancer. In one embodiment, the anti-cancer agent includes, but is not limited to, a targeted antibody, an angiogenesis inhibitor, an alkylating agent, an antimetabolite, a vinca alkaloid, a taxane, a podophyllotoxin, a topoisomerase inhibitor, a hormonal antineoplastic agent and other antineoplastic agents. In one embodiment, the anti-cancer agent is a PD-1 inhibitor, for example, an anti-PD1 antibody.

In one embodiment, the anti-cancer agents that can be used in methods described herein include, but are not limited to, paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan, cytarabine, etoposide, daunorubicin, bleomycin, mitomycin and adriamycin and a combination thereof.

In one embodiment, the anti-cancer agent and Compound (I), or the tartrate salt (e.g., 1:1 Compound (I) tartrate salt), crystal form or pharmaceutical composition described herein are administered contemporaneously. When administered contemporaneously, the anti-cancer agent and the compound can be administered in the same formulation or in different formulations. Alternatively, the compound and the additional anti-cancer agent are administered separately at different times.

The following examples are intended to be illustrative and are not intended to be limiting in any way to the scope of the disclosure.

EXPERIMENTAL

Abbreviations $^1$H proton
aq. aqueous
br. broad
DCM dichloromethane
DVS Dynamic vapour sorption
Equiv equivalent
h hours
HPLC high performance liquid chromatography
IPA isopropanol
LC-MS liquid chromatography coupled to mass spectroscopy
MeOH methanol
min minutes
NMR nuclear magnetic resonance
PLM polarized light microscopy
RH relative humidity
rt room temperature
TGA thermogravimetric analysis
THF tetrahydrofuran
UPLC ultra performance liquid chromatography
XRPD X-ray powder diffraction Analysis Conditions X-Ray Powder Diffraction (XRPD)

XRPD analysis was carried out using a Bruker D8 Advance X-ray powder diffractometer. Parameters for XRPD are listed below.

| Parameters for Reflection Mode | |
|---|---|
| X-ray wavelength | Cu Kα, 1.54179 Å, |
| X-ray tube setting | 40 kV, 40 mA |
| Scan Scope (°2θ) | 4-40 |
| Sample rotation speed | 15 rpm |
| Scan rate | 10 deg./min |

Thermo-Gravimetric Analysis (TGA)

2-5 mg of material was weighted into an open platinum pan and loaded into a TA Q5000IR thermo-gravimetric analyzer. The sample was then heated at a rate of 10° C./min from 25° C. to 350° C./400° C.

Differential Scanning Calorimetry (DSC)

0.5-1 mg of material was weighted into an aluminum DSC pan and sealed non-hermetically with an aluminum lid. The sample pan was then loaded into a TA Instruments Q2000. Once a stable heat-flow response was obtained at 25° C., the sample and reference were heated to 350° C. at a rate of 10° C./min and the resulting heat flow response was monitored.

$^1$H-Nuclear Magnetic Resonance Spectroscopy ($^1$H-NMR)

Nuclear magnetic resonance measurements were recorded on a Bruker Avance DRX 400 instrument at 400 MHz and rt, using DMSO-$d_6$ or $CD_3OD$ as solvent without internal standard.

HPLC/UPLC Methods

A representative method used for solubility measurement is summarized in Table 1. A representative method used for stability evaluation is summarized Table 2.

TABLE 1

UPLC method used for solubility measurement

| | | | |
|---|---|---|---|
| Column details | ACQUITY UPLC ® HSS PFP 1.8 μm, 2.1 * 100 mm | | |
| Column temperature | 60° C. | | |
| Mobile phase A | 0.05% TFA in water | | |
| Mobile phase B | Acetonitrile | | |
| Flow rate | 0.8 mL/min | | |
| Gradient profile | Time (min) | % Mobile Phase A | % Mobile Phase B |
| | 0.00 | 90 | 10 |
| | 4.00 | 10 | 90 |
| | 5.00 | 10 | 90 |
| | 6.5 | 90 | 10 |
| Detector wavelength | 235 nm | | |
| Injection volume | 0.5 μL | | |
| Needle wash solvent | Acetonitrile/Water | | |
| Dilution | Acetonitrile/Water (50/50, v/v) | | |

TABLE 2

HPLC method used for stability evaluation

| | | | |
|---|---|---|---|
| Column details | Waters XBridge Phenyl (150 * 4.6 mm, 3.5 μm) | | |
| Column temperature | 30° C. | | |
| Mobile phase A | 0.05% TFA in water | | |
| Mobile phase B | 0.05% TFA in ACN | | |
| Flow rate | 1.5 mL/min | | |
| Gradient profile | Time (min) | % Mobile Phase A | % Mobile Phase B |
| | 0.00 | 95 | 5 |
| | 20 | 5 | 95 |
| | 20.01 | 95 | 5 |
| | 27 | 95 | 5 |
| Detector wavelength | 235 nm | | |
| Injection volume | 5 μL | | |
| Needle wash solvent | Acetonitrile/Water | | |
| Dilution | Acetonitrile/Water (50/50, v/v) | | |

Example 1: Initial Salt Screen

An initial salt screen was performed using HCl, $H_2SO_4$, and $H_3PO_4$ at either 1 or 2 equivalents in a mixture of DCM and MeOH (2:1).

Approximately 100 mg of 4-amino-5-(6-(4-methylpiperazin-1-yl)-1H-benzo[d]-imidazol-2-yl)thieno[2,3-b]pyridin-6(7H)-one (I) was dissolved in a 2:1 mixture of DCM and MeOH at 50° C. Either 1 or 2 equivalents of acid were added and the resulting solution was stirred at rt for 3 days and the resulting salt samples were analyzed by XRPD.

Salts with weak crystallinity were obtained using HCl (1 equiv), $H_2SO_4$ (2 equiv) and $H_3PO_4$ (1 equiv). Amorphous salts were obtained using HCl (2 equiv) and $H_2SO_4$ (1 equiv). The diffractogram of the mono HCl salt (batch 1) is shown in FIG. 1.

Example 2: Extended Salt Screen

An extended salt screen was performed using $H_3PO_4$, methanesulfonic acid, p-toluenesulfonic acid, citric acid, malic acid, fumaric acid, lactic acid, tartaric acid, succinic acid, benzoic acid and maleic acid at 0.5, 1 and/or 2 equivalents in a mixture of THF and MeOH (2:1). A total of 16 salts were prepared and the results were summarized in Table 3.

Approximately 100 mg of 4-amino-5-(6-(4-methylpiperazin-1-yl)-1H-benzo[d]imidazol-2-yl)thieno[2,3-b]pyridin-6(7H)-one (I) was dissolved in a 2:1 mixture of THF and MeOH at 50° C. 0.5, 1, or 2 equivalents of acid was added and the resulting solution was stirred at rt overnight. Samples affording solids were centrifuged and samples that did not exhibit precipitation were allowed to dry at rt. All samples were characterized by $^1$H NMR, PLM and XRPD.

Figure 2:
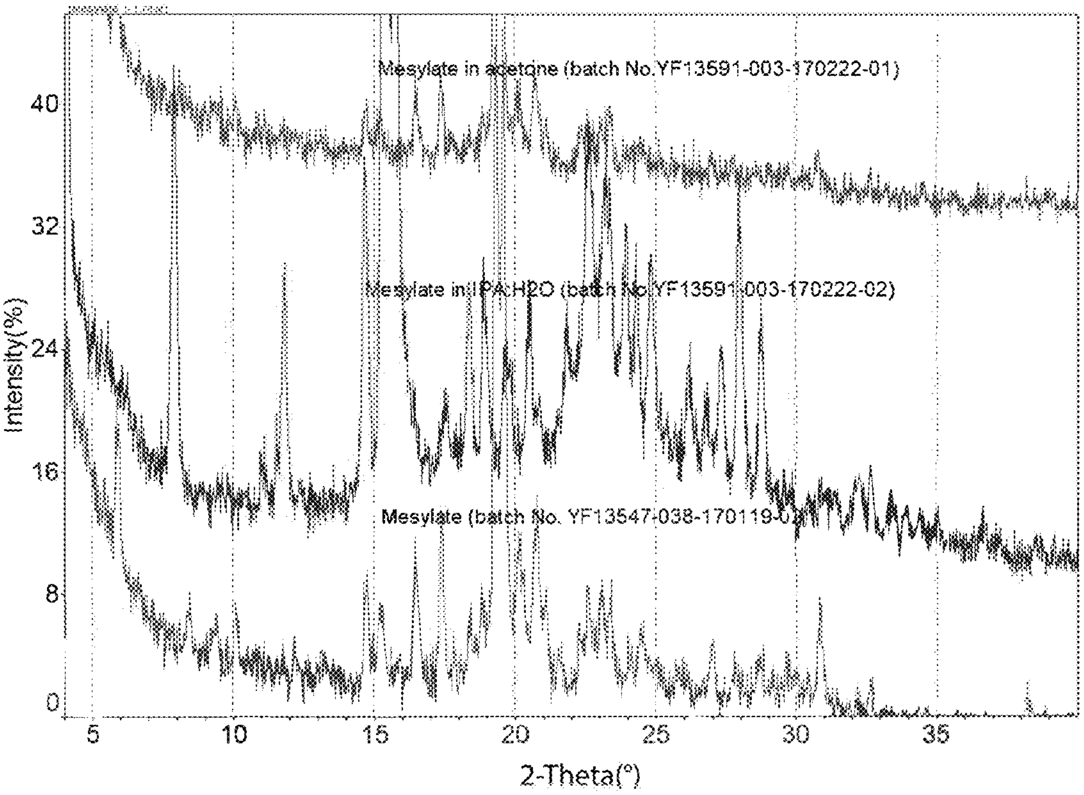
FIG. 2 shows the X-ray Powder Diffraction (XRPD) pattern of 1:1 Compound (I) mesylate salt obtained from different examples. The bottom spectrum is for the mesylate obtained from Example 2 (Batch 1). The middle spectrum is for the mesylate obtained from Example 3 using IPA:water (Batch 2). The top spectrum is for the mesylate obtained from Example 3 using acetone (Batch 3).
Figure 3:
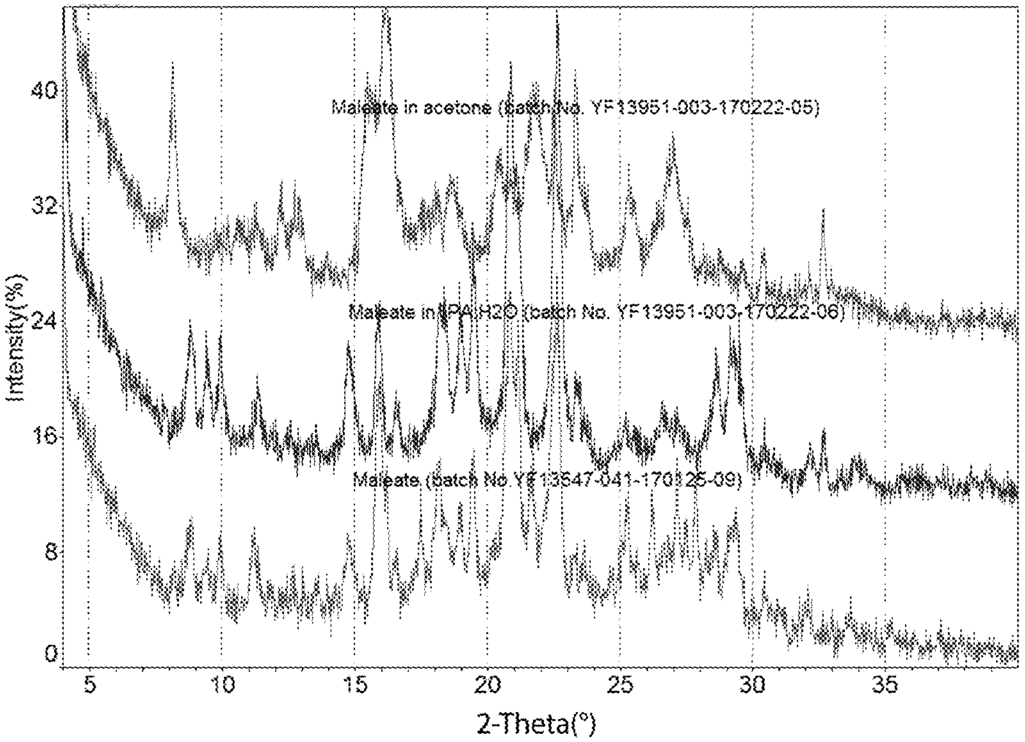
FIG. 3 shows the X-ray Powder Diffraction (XRPD) pattern of 1:1 Compound (I) maleate salt obtained from different examples. The bottom spectrum is for the maleate obtained from Example 2 (Batch 1). The middle spectrum is for the maleate obtained from Example 3 using IPA:water (Batch 2). The top spectrum is for the maleate obtained from Example 3 using acetone (Batch 3).

All 16 salts isolated exhibited different degrees of birefringence. However, only 1:1 mesylate, 1:1 maleate, and 1:1 tartrate salts showed modest to good crystallinity by XRPD. The diffractograms of 1:1 mesylate (batch 1) and 1:1 maleate (batch 1) prepared using this method are shown in FIG. 2 and FIG. 3, respectively. Notably, as shown in Table 3 below, 0.5 equivalent of tartaric acid did not result in the desired hemi tartrate salt (1:0.5) and it was therefore not pursued further.

TABLE 3

16 Salts prepared using 11 pharmaceutically acceptable acids in the extended salt screen

| | | Acid: Compound (I) molar ratio | |
|---|---|---|---|
| Entry | Acid | Used in the experiment | Salt isolated |
| 1 | Phosphoric acid | 1.05:1 | 1.0:1 |
| 2 | Methanesulfonic acid | 1.05:1 | 0.9:1 |
| 3 | Methanesulfonic acid | 2.1:1 | 2:1 |
| 4 | p-Toluenesulfonic acid | 1.05:1 | 0.9:1 |
| 5 | p-Toluenesulfonic acid | 2.1:1 | 2.1:1 |
| 6 | Citric acid | 1.05:1 | 1.0:1 |
| 7 | Citric acid | 0.55:1 | 0.6:1 |
| 8 | L-Malic acid | 1.05:1 | 1.0:1 |
| 9 | Fumaric acid | 1.05:1 | 1.1:1 |
| 10 | Fumaric acid | 0.53:1 | 0.5:1 |
| 11 | Lactic acid | 1.05:1 | 1.0:1 |
| 12 | L-Tartaric acid | 1.05:1 | 1.0:1 |
| 13 | L-Tartaric acid | 0.53:1 | 0.7:1 |
| 14 | Succinic acid | 1.05:1 | 1.0:1 |
| 15 | Benzoic acid | 1.05:1 | 1.1:1 |
| 16 | Maleic acid | 1.05:1 | 1.1:1 |

Example 3: Preparation of Selected Salts

Hydrochloric, mesylate, tartrate and maleate salts were prepared individually using 2 different solvent systems: acetone and IPA/water (95:5).

Approximately 100 mg of 4-amino-5-(6-(4-methylpiperazin-1-yl)-1H-benzo[d]imidazol-2-yl)thieno[2,3-b]pyridin-6(7H)-one (I) was suspended in acetone (2 mL) or IPA/water (95:5, 2 mL). The suspension was stirred at 50° C. Acid (1 equiv, 0.5 mol/L) was added and the mixture was stirred overnight. The salt was then isolated and dried at 30° C. under vacuum. The obtained salts were characterized by TGA, DSC and XRPD.

The two solvent systems yielded different polymorphic forms of hydrochloric (IPA: batch 2; Acetone: batch 3), mesylate (IPA: batch 2; Acetone: batch 3), and maleate salts (IPA: batch 2; Acetone: batch 3). The diffractograms of the polymorphic forms of HCl, mesylate and maleate salts isolated are shown in FIG. 1, FIG. 2, and FIG. 3, respectively. As demonstrated in the XRPD diffractograms, the crystallinity of the mesylate and maleate salts is moderate.

One polymorphic form of 1:1 Compound (I) tartrate salt was isolated using the two solvent systems described in Example 3.

Figure 4:
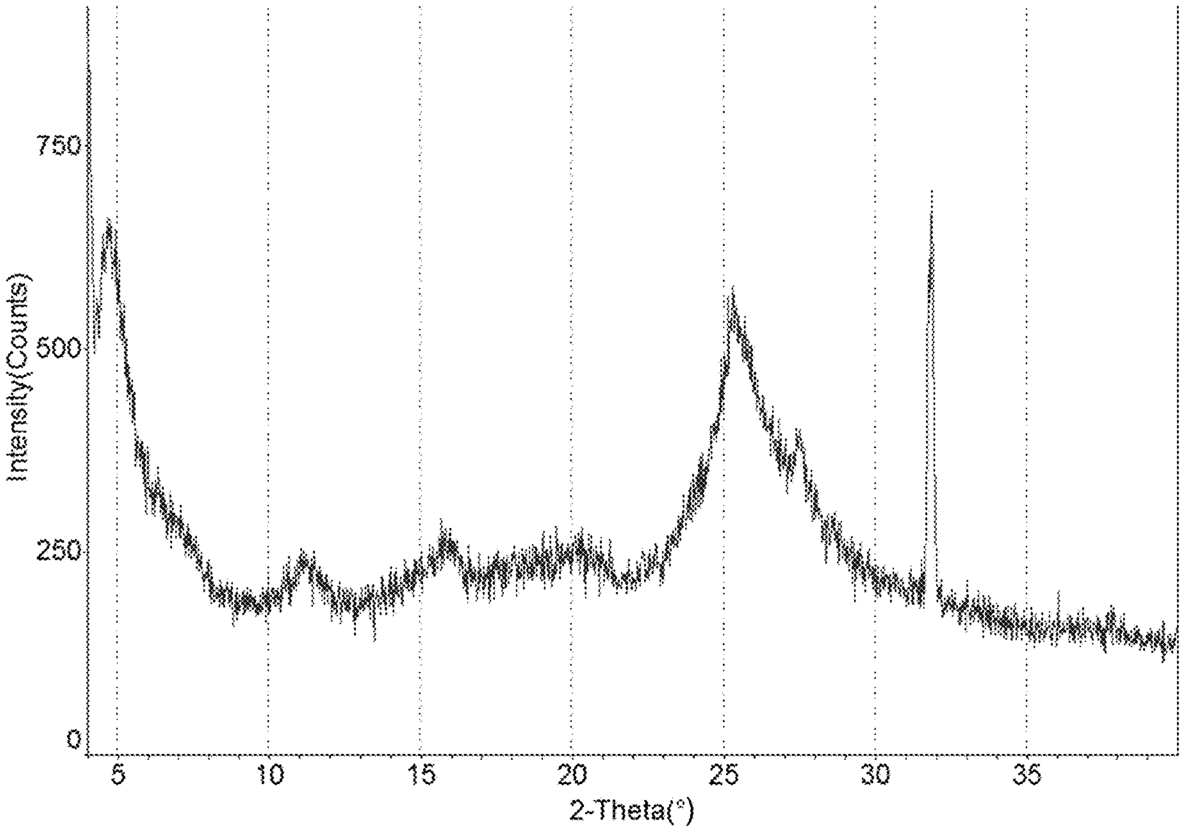
FIG. 4 shows the X-ray Powder Diffraction (XRPD) pattern of 1:2 Compound (I) di-hydrochloride salt.

Example 4: Preparation of 4-amino-5-(6-(4-methylpiperazin-1-yl)-1H-benzo[d]imidazol-2-yl)thieno[2,3-b]pydidin-6(7H)-one (I) Di-Hydrochloride Approximately 15 g (40.95 mmol) of 4-amino-5-(6-(4-methylpiperazin-1-yl)-1H-benzo[d]imidazol-2-yl)thieno[2,3-b]pyridin-6(7H)-one (I) was suspended in a mixture of DCM (300 mL) and MeOH (450 mL). 2M HCl in $Et_2O$ (45 mL, 90.15 mmol) was added slowly at rt. The resulting mixture was stirred at rt for 60 min. Solvent was then removed in vacuo, and the resulting solid was triturated with $Et_2O$ (120 mL) and filtered to give the di-HCl salt as a brown solid. The di-HCl salt was characterized by XRPD and NMR The XRPD diffractogram is shown in FIG. 4, which indicates that the crystallinity of the obtained di-HCl salt was very low.

Figure 5:
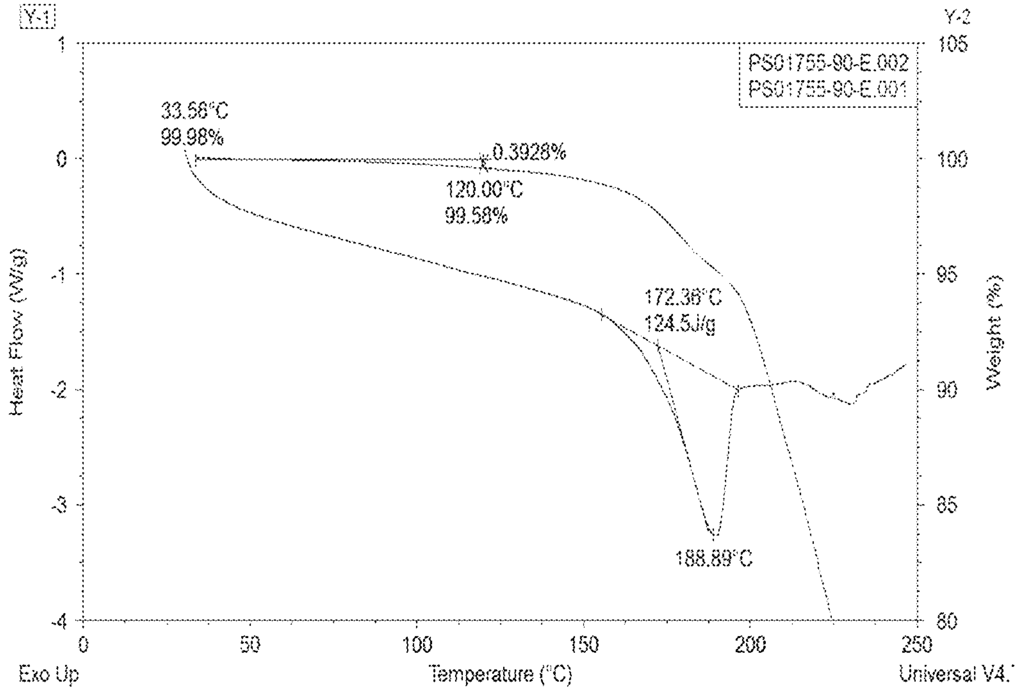
FIG. 5 shows the Thermogravimetric Analysis (TGA) and Differential Scanning Calorimetry Analysis (DSC) thermograms of 1:1 Compound (I) tartrate salt obtained from Example 5.

Example 5: Preparation of 4-amino-5-(6-(4-methylpiperazin-1-yl)-1H-benzo[d]imidazol-2-yl)thieno[2,3-b]pyridin-6(7H)-one (I) tartrate 4-amino-5-(6-(4-methylpiperazin-1-yl)-1H-benzo[d]imidazol-2-yl)thieno[2,3-b]pyridin-6(7H)-one (4.5 kg) was dissolved in an aq. acetic acid solution (44 kg of water, 1.78 kg of acetic acid) at 55 to 60° C. The solution was stirred for 15 to 120 min. In a separate reactor, an aq. solution of L-(+)-tartaric acid was prepared by adding the acid (1.98 kg) to water (14-18 kg) at 20 to 30° C. and the solution was stirred for 15 to 60 min. The acetic acid solution containing Compound (I) was then added to the aqueous solution of L-(+)-tartaric acid slowly at 55 to 60° C. Optionally, seed crystals were added. The resulting mixture was allowed to crystallize at 55 to 60° C. for 12 to 24 h. The mixture was then cooled to at 20 to 25° C. and stirred for 8 to 16 h. The precipitated product was then collected and washed with ethanol and dried at 40 to 60° C. for 3 to 24 h under vacuum to give the desired product. The title compound was characterized by 1H NMR, DSC, TGA and XRPD. The DSC and TGA results are shown in FIG. 5. The XRPD diffractogram is shown in FIG. 6, and the results are tabularized in Table 4.

TABLE 4

List of major peaks and their relative intensity in the XRPD diffractogram of 4-amino-5-(6-(4-methylpiperazin-1-yl)-1H-benzo[d]imidazol-2-yl)thieno[2,3-b]pyridin-6(7H)-one tartrate salt (1:1 Compound (I) tartrate salt)

| Angle (2θ) | Relative intensity (%) |
|---|---|
| 8.7 | 7.2 |
| 11.9 | 49.9 |
| 12.9 | 3.0 |
| 14.0 | 33.6 |
| 15.4 | 64.2 |
| 16.9 | 100 |
| 17.2 | 49.6 |
| 22.1 | 28.7 |
| 25.6 | 41.2 |

TABLE 4-continued

List of major peaks and their relative intensity in the XRPD diffractogram of 4-amino-5-(6-(4-methylpiperazin-1-yl)-1H-benzo[d]imidazol-2-yl)thieno[2,3-b]pyridin-6(7H)-one tartrate salt (1:1 Compound (I) tartrate salt)

| Angle (2θ) | Relative intensity (%) |
|---|---|
| 26.3 | 26.9 |
| 30.7 | 29.1 |
| 34.0 | 28.7 |

1H NMR (400 MHz, DMSO-d8): 12.65 (br s, 1H), 10.65 (br s, 1H), 8.00 (br s, 1H), 7.68 (d, J=5.6 Hz, 1H), 7.49 (br s, 1H), 7.20-7.17 (m, 2H), 6.92 (d, J=2.5 Hz, 1H), 6.71 (br, s, 4H), 4.16 (s, 2H), 3.22 (br s, 4H), 2.88 (br s, 4H), 2.52 (s, 3H).

Example 6: Hygroscopicity Measurements of 4-amino-5-(6-(4-methylpiperazin-1-yl)-1H-benzo[d]imidazol-2-yl)thieno[2,3-b]pyridin-6(7H)-one (I) and Its Salts The compound to be tested is submitted to hygroscopicity test by means of a DVS apparatus. The testing parameters are in Table 5. The hygroscopicity measurement results are shown in Table 6.

TABLE 5

Parameters used in a DVS apparatus

| | | |
|---|---|---|
| Total gas flow (sccm) | | 200 |
| Oven temperature (° C.) | | 25 |
| Solvent | | Water |
| Control Mode | | Open loop |
| Method | Preheat | N/A |
| | Dry | 2 hours with $N_2$ (0% RH) |
| | Stage | Mode DMDT |
| | method | Cycle: 0% RH-90% RH-0% RH |
| | | Stage Step: 10% |
| | | Dm/dt criteria: <0.01%/min |
| | | sampling rate: 1 sec |
| | | minimum duration: 10 min |
| | | maximum duration: 180 min |

TABLE 6

Hygroscopicity measurement results

| | Change in Mass (%) | | |
|---|---|---|---|
| Compound | Water uptake at 30% RH | Water uptake at 60% RH | Water uptake at 90% RH |
| Free base | 0.5 | 0.9 | 26 |
| Tartrate salt | 0.06 | 0.3 | 0.7 |
| Mono HCl salt (Batch 3) | 3.7 | 6.1 | 38.3 |

Example 7: Solubilities of 4-amino-5-(6-(4-methylpiperazin-1-yl)-1H-benzo[d]imidazol-2-yl)thieno[2,3-b]pyridin-6(7H)-one (1) and Its Salts The compounds to be tested were prepared in 3 different media as described below.

Samples prepared in water: approximately 30-40 mg of test material was weighted into a glass vial. 1 mL of water was added. The sample was stirred for 1 h at ambient temperature and the sample was analyzed by HPLC at 24 h.

Samples prepared in simulated gastric fluid (SGF) buffer: approximately 40 mg of test material was weighted into a glass vial. 4 mL of SGF buffer was added to make a target concentration at 10 mg/mL. The sample was stirred for 24 h at 37° C. and the sample was analyzed by HPLC at 24 h.

Samples prepared in fasted state simulated intestinal fluid (FaSSIF) buffer: approximately 8 mg of test material was weighted into a glass vial. 4 mL of FassiF buffer was added to make a target concentration at 2 mg/mL. The sample was stirred for 24 h at 37° C. and the sample was analyzed by HPLC at 24 h.

The samples were stirred for 1 h at ambient temperature or 24 h at 37° C. The samples were then centrifuged and the resulting supernatants were analyzed by HPLC to determine the solubility. The solubilities of Compound (I) and its salts in different media were summarized in Table 7.

TABLE 7

Solubilities of Compound (I) and its salts in different media

| Compound | Solubility (mg/mL) water | SGF | FaSSIF |
|---|---|---|---|
| Free base | 0.3 | 0.5 | 0.09 |
| Tartrate salt | — | 9.0 | 0.02 |
| Mono HCl salt, Batch 3 | 10.2 | 9.0 | 0.22 |
| Di-HCl salt | 3.3 | — | — |

Example 8: Stability of 4-amino-5-(6-(4-methylpiperazin-1-yl)-1H-benzo[d]imidazol-2-yl)thieno[2,3-b]pyridin-6(7H)-one (I) tartrate Purity and stability of 4-amino-5-(6-(4-methylpiperazin-1-yl)-1H-benzo[d]imidazol-2-yl)thieno[2,3-b]pyridin-6(7H)-one (I) tartrate have been tested. Stability samples were prepared and stored under 3 different storage conditions: 2-8° C./ambient RH, 25° C./60% RH, and 40° C./75% RH. Stability samples were removed from their storage conditions within each pull window, and the samples were allowed to equilibrate to ambient conditions prior to analysis. The appearance was evaluated by visual inspection, purity and total amount of impurities were analyzed by HPLC and crystalline form was characterized by XRPD. The results are summarized in Table 8.

TABLE 8

Long term stability data for 4-amino-5-(6-(4-methylpiperazin-1-yl)-1H-benzo[d]imida-zol-2-yl)thieno[2,3-b]pyridin-6(7H)-one tartrate salt (1:1 Compound (I) tartrate salt)

| Storage condition | Parameter | Initial | 1 month | 3 month | 6 month | 12 month |
|---|---|---|---|---|---|---|
| 5° C./ambient RH | Appearance | Light brown solid | Light brown solid | Light brown solid | Light brown solid | Light brown solid |
| | Total amount of impurities | 0.03% | 0.03% | 0.0% | 0.03% | 0.03% |
| | Purity | 100% | 100% | 100% | 100% | 100% |
| | Crystalline form | Yes | Not tested | Not tested | Not tested | Same as the initial stage |

TABLE 8-continued

Long term stability data for 4-amino-5-(6-(4-methylpiperazin-1-yl)-1H-benzo[d]imida-zol-2-yl)thieno[2,3-b]pyridin-6(7H)-one tartrate salt (1:1 Compound (I) tartrate salt)

| Storage condition | Parameter | Initial | 1 month | 3 month | 6 month | 12 month |
|---|---|---|---|---|---|---|
| 25° C./60% RH | Appearance | Light brown solid | Light brown solid | Light brown solid | Light brown solid | Light brown solid |
| | Total amount of impurities | 0.03% | 0.02% | 0.03% | 0.03% | 0.03% |
| | Purity | 100% | 100% | 100% | 100% | 100% |
| | Crystalline form | Yes | Not tested | Not tested | Not tested | Same as the initial stage |
| 40° C./75% RH | Appearance | Light brown solid | Light brown solid | Light brown solid | Light brown solid | Light brown solid |
| | Total amount of impurities | 0.03% | 0.02% | 0.03% | 0.03% | 0.03% |
| | Purity | 100% | 100% | 100% | 100% | 100% |
| | Crystalline form | Yes | Not tested | Not tested | Not tested | Same as the initial stage |

Example 9: Pharmacokinetic analyses of 4-amino-5-(6-(4-methylpiperazin-1-yl)-1H-benzo[d]imidazol-2-yl)thieno[2,3-b]pyridin-6(7H)-one (I) and its salts A single dose as powder in capsule of Compound (I), 1:1 Compound (I) mono HCl salt (Batch 3), di-HCl salt of Compound (I), and 1:1 Compound (I) tartrate salt was administrated to male Beagle dogs at either 125 mg/kg or 150 mg/kg. Blood samples were collected for up to 24 h and the plasma was analyzed for Compound (I) plasma level by LC/MS. The results are shown in Table 9.

TABLE 9

Pharmacokinetic parameters after oral administration of 4-amino-5-(6-(4-methylpiperazin-1-yl)-1H-benzo[d]imidazol-2-yl)thieno[2,3-b]pyridin-6(7H)-one (Compound (I)) and its salts to beagle dogs

| Solid form | Free base | Mono HCl (Batch 3) | Di-HCl | Tartrate |
|---|---|---|---|---|
| Oral Dose (mg/kg) | 125 | 125 | 125 | 150 |
| $C_{max}$ (ng/mL) | 301 | 547 | 530 | 514 |
| $AUC_{0-tlast}$ (ng · h/mL) | 2264 | 4354 | 6862 | 6550 |

The invention claimed is:

1. A tartrate salt of Compound (I) represented by the following structural formula:

(I)

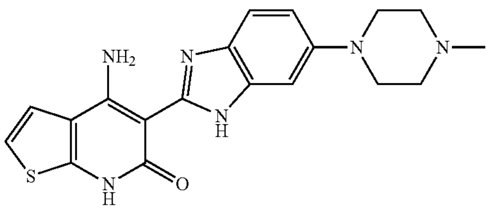

, wherein the molar ratio between Compound (I) and tartaric acid is 1:1, wherein the tartrate salt is in a single crystalline form, characterized by an X-ray powder diffraction pattern which comprises at least three peaks chosen from 11.9°, 15.4°, 16.9°, 17.2°, and 25.6°±0.2 in 2θ.

2. The tartrate salt of claim 1, wherein the tartrate salt is in a single crystalline form, characterized by an X-ray powder diffraction pattern which comprises peaks at 11.9°, 14.0°, 15.4°, 16.9°, 17.2°, 25.6°, 26.3°, and 30.7°=0.2 in 2θ.

3. The tartrate salt of claim 1, wherein the tartrate salt is in a single crystalline form, characterized by an X-ray powder diffraction pattern which comprises peaks at 11.9°, 14.0°, 15.4°, 16.9°, 17.2°, 22.1°, 25.6°, 26.3°, 30.7°, and 34.0°±0.2 in 2θ.

4. The tartrate salt of claim 1, wherein the tartrate salt is in a single crystalline form, characterized by an X-ray powder diffraction pattern which further comprises peaks at 8.7° and 12.9°±0.2 in 2θ.

5. The tartrate salt of claim 1, wherein the tartrate salt is in a single crystalline form, characterized by a differential scanning calorimeter (DSC) peak phase transition temperature of 189±2° C.

6. The tartrate salt of claim 1, wherein water uptake is less than 4% of the mass of the tartrate salt at 90% relative humidity (RH) as measured under the following conditions:

i) drying between 0.5 and 1.5 mg of the tartrate salt under a nitrogen atmosphere at 0% relative humidity for 2 hours;

ii) increasing or decreasing the relative humidity in steps of 10% from 0% to 90% then to 0%;

iii) maintaining the relative humidity at each step until the mass change compared to the mass of the original tartrate salt per minute is less than 0.01 (%/min), provided that minimum and maximum duration time at each step is 10 minutes and 180 minutes, respectively; and iv) measuring the mass of the tartrate salt at 90% relative humidity and wherein steps i)-iv) are carried out at 25° C.

7. The tartrate salt of claim 6, wherein water uptake is less than 1% of the mass of the tartrate salt at 90% relative humidity (RH).

8. The tartrate salt of claim 1, wherein water uptake is less than 1% of the mass of the tartrate salt at 30% relative humidity (RH) as measured under following conditions:

i) drying between 0.5 and 1.5 mg of the tartrate salt under a nitrogen atmosphere at 0% relative humidity for 2 hours;

ii) increasing or decreasing the relative humidity in steps of 10% from 0% to 90% then to 0%;

iii) maintaining the relative humidity at each step until the mass change compared to the mass of the original tartrate salt per minute is less than 0.01 (%/min), provided that minimum and maximum duration time at each step is 10 minutes and 180 minutes, respectively; and iv) measuring the mass of the tartrate salt at 30% relative humidity and wherein steps i)-iv) are carried out at 25° C.

9. The tartrate salt of claim 8, wherein water uptake is less than 0.1% of the mass of the tartrate salt at 30% relative humidity (RH).

10. A solid pharmaceutical composition comprising the tartrate salt of claim 1, and a pharmaceutically acceptable carrier or diluent.

11. A method of treating a subject with cancer, comprising administering to the subject an effective amount of the tartrate salt of claim 1, wherein the cancer is breast cancer, colorectal cancer, lung cancer, ovarian cancer, uterine cancer, prostate cancer, leukemia, lymphomas, brain cancer, head and neck cancer, pancreatic cancer, melanoma, hepatocellular carcinoma, or renal cancer.

12. A method of treating a subject with cancer, comprising administering to the subject an effective amount of the tartrate salt of claim 1, and an effective amount of second anti-cancer agent, wherein the cancer is breast cancer, colorectal cancer, lung cancer, ovarian cancer, uterine cancer, prostate cancer, leukemia, lymphomas, brain cancer, head and neck cancer, pancreatic cancer, melanoma, hepatocellular carcinoma, or renal cancer;

wherein the second anti-cancer agent is ipilumab, nivolumab, pembrolizumab, pidilizumab, BMS 936559, MPDL3280A, MSB0010718C, MED14736, paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan, cytarabine, etoposide, daunorubicin, bleomycin, mitomycin, or adriamycin.

* * * * *